United States Patent
Choi et al.

(10) Patent No.: US 9,593,353 B2
(45) Date of Patent: Mar. 14, 2017

(54) MICROORGANISMS FOR PRODUCTION OF O-SUCCINYLHOMOSERINE AND METHOD FOR PRODUCTION OF O-SUCCINYLHOMOSERINE USING THE SAME

(71) Applicant: CJ CHEILJEDANG CORPORATION, Seoul (KR)

(72) Inventors: Su Jin Choi, Daegu (KR); So Young Kim, Gyeonggi-do (KR); Chang Il Seo, Incheon (KR); Yong Uk Shin, Gyeonggi-do (KR); Young Lyeol Yang, Gyeonggi-do (KR); Hye Won Um, Gyeonggi-do (KR); Hye Min Park, Gyeongsangnam-do (KR); Sung Hoo Jhon, Seoul (KR); Byung Hoon Jung, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/031,703

(22) PCT Filed: Oct. 22, 2014

(86) PCT No.: PCT/KR2014/009968
§ 371 (c)(1),
(2) Date: Apr. 22, 2016

(87) PCT Pub. No.: WO2015/060648
PCT Pub. Date: Apr. 30, 2015

(65) Prior Publication Data
US 2016/0304918 A1    Oct. 20, 2016

(30) Foreign Application Priority Data
Oct. 23, 2013 (KR) .................. 10-2013-0126606

(51) Int. Cl.
*C12P 13/06* (2006.01)
*C12N 9/10* (2006.01)

(52) U.S. Cl.
CPC ............ *C12P 13/06* (2013.01); *C12N 9/1029* (2013.01); *C12Y 203/01046* (2013.01); *Y02P 20/52* (2015.11)

(58) Field of Classification Search
None
See application file for complete search history.

(56) References Cited

U.S. PATENT DOCUMENTS 7,851,180 B2 * 12/2010 Shin ..................... C12N 9/1029
                                                435/252.1

FOREIGN PATENT DOCUMENTS

| KR | 1020080011132 A | 1/2008 |
| KR | 1020090106365 A | 10/2009 |

OTHER PUBLICATIONS

Ishii et al., "Complete Genome Sequence of the Denitrifying and N2O-Reducing Bacterium *Pseudogulbenkiania* sp. Strain NH8B", Journal of Bacteriology, Nov. 2011, 193(22), p. 6395-6396. doi:10.1128/JB.06127-11.*

NCBI Reference Sequence: WP_008952231.1, "Multispecies: homoserine O-acetyltransferase [Pseudogulbenkiania]," May 10, 2013, one page.

* cited by examiner

*Primary Examiner* — Suzanne M Noakes

(57) ABSTRACT

The present invention relates to a polypeptide having a resistant to feedback inhibition by methionine and an activity of homoserine O-succinyltransferase, a O-succinyl homoserine-producing microorganism expressing the polypeptide, and a method for producing O-succinyl homoserine using the same.

10 Claims, No Drawings

MICROORGANISMS FOR PRODUCTION OF O-SUCCINYLHOMOSERINE AND METHOD FOR PRODUCTION OF O-SUCCINYLHOMOSERINE USING THE SAME

CROSS-REFERENCES TO RELATED APPLICATIONS

This application is a U.S. national phase application of International PCT Patent Application No. PCT/KR2014/009968, which was filed on Oct. 22, 2014, which claims priority to Korean Patent Application No. 10-2013-0126606, filed Oct. 23, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_044_00US_SeqList_ST25.txt. The text file is 10 KB, was created on Apr. 22, 2016, and is being submitted electronically via EFS-Web.

TECHNICAL FIELD

The present invention relates to an isolated polypeptide which has a resistance to feedback inhibition by methionine and a homoserine O-succinyltransferase activity, a microorganism expressing the polypeptide, and a method for producing O-succinylhomoserine using the same.

BACKGROUND ART

Most microorganisms present in nature are known to utilize O-succinylhomoserine or O-acetylhomoserine as an intermediate for the biosynthesis of methionine. Generally, O-succinylhomoserine is produced by homoserine O-succinyltransferase (MetA) which conjugates the succinyl group of succinyl-coA to homoserine, and O-acetylhomoserine is produced by homoserine O-acetyltransferase (MetX) which conjugates acetyl group of acetyl-coA to homoserine. That is, in producing O-succinylhomoserine among intermediates, metA is one of the most important genes in the development of microorganisms producing the same. Meanwhile, unlike MetA, MetX is known to be not feedback inhibited and have high enzyme stability.

O-succinylhomoserine is accumulated when cystathionine gamma synthase in the methionine biosynthesis pathway is blocked, and thus the O-succinylhomoserine-producing strain requires L-methionine. Accordingly, methionine is added to a medium, and the activity of homoserine O-succinyltransferase is inhibited by the methionine added to the medium, and eventually, O-succinylhomoserine cannot be obtained at high concentration.

Accordingly, many prior patents have focused their studies on the release of feedback inhibition of metA from a feedback control system. However, the homoserine O-succinyltransferase encoded by metA has problems in that it has low stability by its wild type protein itself and that the introduction of a mutation for the release of feedback inhibition worsens the instability. Accordingly, for the development of a O-succinylhomoserine-producing strain with high productivity, it is necessary that the feedback inhibition of the metA gene be removed and the enzyme stability be secured

DISCLOSURE

Technical Problem

In order to solve the phenomenon of feedback inhibition of metA and the enzyme instability problem described above, the present inventors have endeavored to develop a homoserine O-succinyltransferase, which has secured enzyme stability while not being feedback inhibited by methionine, and in this regard, screened novel enzymes having the activity. As a result of selecting the thus-screened candidate genes and culturing in a flask after introducing them into *Escherichia* sp., the present inventors have discovered the production of O-succinylhomoserine, and that the thus-selected genes have a homoserine O-succinyltransferase activity and a resistance to feedback inhibition by methionine, thereby completing the present invention.

Technical Solution

An object of the present invention is to provide a novel isolated polypeptide having a resistance to the feedback inhibition by methionine and a homoserine O-succinyltransferase activity.

Another object of the present invention is to provide a polynucleotide encoding the novel isolated polypeptide.

A further object of the present invention is to provide a microorganism for producing O-succinylhomoserine, which expresses the novel isolated polypeptide.

A further object of the present invention is to provide a method for producing O-succinylhomoserine using the above microorganism.

Advantageous Effects of the Invention

The microorganism for producing O-succinylhomoserine including a novel isolated polypeptide, which has a resistance to the feedback inhibition by methionine and a homoserine O-succinyltransferase activity, can have a resistance to the feedback inhibition by methionine and produce O-succinylhomoserine with high yield, and thus can be effectively used for the production of L-methionine, which uses the same as the precursor, with high yield.

BEST MODE FOR CARRYING OUT THE INVENTION

In order to achieve the above objects, in an aspect, the present invention provides a novel isolated polypeptide which has a resistance to feedback inhibition by methionine and a homoserine O-succinyltransferase activity.

As used herein, the term "homoserine O-succinyltransferase activity" refers to the activity of converting homoserine into O-succinylhomoserine.

As used herein, the term "feedback inhibition" refers to the inhibition of the activity of homoserine O-succinyltransferase by methionine.

The polypeptide of the present invention is characterized in that it has an amino acid sequence of SEQ ID NO: 1 having the homoserine O-succinyltransferase activity, and a resistance to feedback inhibition by methionine. Any polypeptide that shares a sequence homology of 80% or greater to the above polypeptide, specifically 90% or greater, more specifically 95% or greater, and even more specifically 97% or greater is also within the scope of the present invention, insofar as the polypeptide has the homoserine O-succinyltransferase activity and the resistance to the feedback inhibition by methionine suggested in the present invention. The % homology may be determined using BLAST 2.0, which is a reference algorithm, or FASTA by Pearson [Methods Enzymol., 183, 63(1990), infra]. Based on the BLAST algorithm, programs called BLASTN and BLASTX have been developed [www.ncbi.nlm.nih.gov, infra].

In another aspect, the present invention provides an isolated polynucleotide encoding the above polypeptide. Specifically, the polypeptide may be encoded by the polynucleotide sequence of SEQ ID NO: 2 or SEQ ID NO: 3, due to codon degeneracy, those polynucleotides which have a sequence homology of at least 80% to the above sequence, specifically 90% or greater, more specifically 95% or greater, and even more specifically 97% or greater are also within the scope of the present invention, although not limited thereto.

In still another aspect, the present invention provides a vector which includes the polynucleotide in an operable manner.

As used herein, the term "vector" refers to a DNA construct including the nucleotide sequence of the polynucleotide encoding a protein of interest, in which the protein of interest is operably linked to a suitable regulatory sequence so that the protein of interest can be expressed in an appropriate host. The regulatory sequence may include a promoter capable of initiating transcription, any operator sequence for the regulation of the transcription, a sequence encoding an appropriate mRNA ribosome-binding domain, and a sequence regulating the termination of transcription and translation. The vector, after being transformed into an appropriate host, may be replicated or function irrespective of the host genome, or may be integrated into the host genome itself.

The vector used in the present invention may not be particularly limited as long as the vector is replicable in the host, and any vector known in the art may be used.

In still another aspect, the present invention provides an O-succinylhomoserine producing microorganism expressing a polypeptide, which has a resistance to feedback inhibition by methionine and a homoserine O-succinyltransferase activity.

As used herein, the term "an O-succinylhomoserine producing microorganism" may refer to a microorganism which can produce O-succinylhomoserine and store it intracellularly and extracellularly The microorganism for producing O-succinylhomoserine includes prokaryotic- and eukaryotic microorganism strains, e.g., the microorganism strains belonging to the genus *Escherichia*, the genus *Erwinia*, the genus *Serratia*, the genus *Providencia*, the genus *Corynebacterium* and the genus *Brevibacterium*, but not limited thereto. Specifically, the microorganism may be a microorganism belonging to the genus *Escherichia*, for example, *Escherichia coli.*

The O-succinylhomoserine producing microorganism may be prepared using microorganism strains which produce L-lysine, L-threonine, or L-isoleucine, and specifically, using an L-threonine producing strain. Since the L-threonine producing strain is a strain capable of synthesizing L-threonine and homoserine as a precursor of O-succinylhomoserine, a large amount of methionine precursors, i.e., O-succinylhomoserine, can be synthesized using the strain.

In the present invention, the expression of the polypeptide may be achieved by transforming with a recombinant vector which includes a gene encoding the polypeptide in an operable manner or by inserting a polynucleotide encoding the polypeptide into the chromosome, but the methods are not limited thereto.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. The polynucleotide may be inserted in any form insofar as it can be introduced into a host cell and expressed therein. For example, the polynucleotide may be introduced into a host cell in the form of an expression cassette, which is a polynucleotide construct including all essential elements required for self-expression. The expression cassette may conventionally include a promoter operably connected to the open reading frame ("ORF", hereinafter) of the gene, a transcription termination signal, a ribosome-binding domain, and a translation termination signal. The promoter used in the present invention may not be particularly limited as long as it can initiate the transcription of the polynucleotide encoding the target protein in a host cell with high frequency, and any promoter known in the art may be used. Specifically, T7 promoter, trc promoter, tac promoter, and cysK promoter (Korean Pat. No. 10-0966324) may be used, although not limited thereto.

In an exemplary embodiment of the present invention, the metB gene encoding cystathionine gamma synthase in the microorganism may be further deleted or weakened.

In an exemplary embodiment of the present invention, the thrB gene encoding homoserine kinase and the metA gene encoding homoserine O-succinyltransferase in the microorganism may be further deleted or weakened.

In the present invention, the sequences of the genes can be obtained from databases such as The National Center for Biotechnology Information (NCBI).

As used herein, the term "deletion" refers to a type of removal, within the chromosome, of a part or the entirety of a nucleotide sequence region of a target gene from the nucleotide sequence corresponding to the initiation codon to that of the termination codon, or a part or the entirety of the nucleotide sequence region of a regulatory region thereof.

As used herein, the term "weakening" refers to removal or reduction of intracellular activity of at least one enzyme being encoded by the corresponding DNA in a microorganism strain. For example, the expression of a protein may be weakened by modifying the promoter region or the nucleotide sequence of 5'-UTR of a gene, or the activity of a protein may be weakened by introducing a mutation in the ORF region of the corresponding gene.

In another aspect, the present invention provides a method for producing O-succinylhomoserine including culturing the above microorganism in a medium to produce O-succinylhomoserine, and obtaining the O-succinylhomoserine from the microorganism or the medium.

The culturing of the microorganism strain for producing the O-succinylhomoserine prepared above may be performed according to the appropriate medium and conditions for culture known in the art. The culture process may be easily adjusted for use by one of ordinary skill in the art according to the strain to be selected. Specifically, the culture may be a batch culture, a continuous culture, and a fetch culture, but is not limited thereto. These various culture processes are disclosed, for example, in a reference ("*Biochemical Engineering*" by James M. Lee, Prentice-Hall International Editions, pp 138-176).

The media used for culture must appropriately meet the requirements for particular strains. Examples of the media for various microorganisms are disclosed, for example, in a reference ("*Manual of Methods for General Bacteriology*" by the American Society for Bacteriology, Washington D.C., USA, 1981). The media can include various carbon sources, nitrogen sources, and trace elements. Examples of the carbon source to be contained in the media may include carbohydrates such as glucose, sucrose, lactose, fructose, maltose, starch, and cellulose; fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination. Examples of the nitrogen source to be contained in the media may include organic nitrogen sources such as peptone, yeast extract, meat gravy, malt extract, corn steep liquor (CSL), and bean flour; and inorganic nitrogen sources such as urea, ammonium sulfate, ammonium chloride, ammonium phosphate, ammonium carbonate, and ammonium nitrate. These nitrogen sources may be used alone or in combination. As a phosphorous source, the media may include potassium dihydrogen phosphate, dipotassium hydrogen phosphate, and corresponding sodium-containing salts. Additionally, the culture media may include metals such as magnesium sulfate and iron sulfate. Furthermore, amino acids, vitamins, and appropriate precursors, etc., may be included. These culture media or precursors may be added to the culture in the form of a batch culture or continuous culture.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, an oxygen gas or a gas containing an oxygen gas (e.g., air) may be added to a culture to maintain aerobic conditions in the culture. The culture temperature may be in the range from 20° C. to 45° C., and specifically from 25° C. to 40° C. The cultivation may be continued until the desired amount of O-succinylhomoserine product is obtained, and specifically for from 10 hours to 160 hours.

The O-succinylhomoserine produced by the method of the present invention may be converted into methionine by cystathionine gamma synthase or O-succinylhomoserine sulfhydrylase. Additionally, succinic acid may be obtained as a byproduct in addition to L-methionine, by reacting the O-succinyl-L-homoserine produced by the method of the present invention with $CH_3SH$.

In still another aspect, the present invention relates to the use of a polypeptide having a resistance to feedback inhibition by methionine and a homoserine O-succinyltransferase activity, in which the polypeptide has an amino acid sequence of SEQ ID NO: 1. The novel isolated polypeptide of the present invention was confirmed to have a resistance to feedback inhibition by methionine and to be able to produce O-succinylhomoserine with high yield, and thus the polypeptide can be used for producing O-succinylhomoserine.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1

Selection of Polypeptides Having Novel O-Succinyltransferase Activity

As a method of releasing the feedback control of metA gene and securing the stability thereof, metX derived from *Chromobacterium violaceum* has been developed based on the fact that the metX gene (homoserine O-acetyltransferase) is not feedback inhibited by L-methionine although the metX gene has a structure similar to that of metA gene.

In this regard, for the development of a novel homoserine O-acetyltransferase, the present inventors have performed a homology analysis regarding the amino acid sequences of the already-developed metX derived from *Chromobacterium violaceum*, and finally selected the polypeptide having an amino acid sequence of SEQ ID NO: 1, released from the feedback inhibition by methionine. The present inventors have newly confirmed that the selected polypeptide, although it is a metX derived from *Sideroxydans lithotrophicus* ES-1, has a novel activity that has never been reported previously.

Example 2

Plasmid Construction 2-1. Synthesis of metX gene derived from *Pseudogulbenkiania ferrooxidans* 2002

The metX gene derived from *Pseudogulbenkiania ferrooxidans* 2002 (SEQ ID NO: 3) was synthesized based on the metX gene sequence (SEQ ID NO: 2) of the NCBI database (reference sequence: ZP_03696709.1) via a codon optimization process so that the gene can be expressed in *E. coli*.

2-2. Construction of a Plasmid Expressing metX Gene Derived from *Pseudogulbenkiania ferrooxidans* 2002

The metX gene was amplified by PCR using the primers of SEQ ID NOS: 4 and 5 based on the synthesized nucleotide sequence of SEQ ID NO: 3. The primer of SEQ ID NO: 5 has the HindIII restriction site.

```
                                       SEQ ID NO: 4)
5'-ATC ATGTCCACTACAGAATCCTCG-3'

SEQ ID NO: 5)
5'-CCC AAGCTT ttatgccgccacttctttggc-3'
```

The PCR was performed for 30 cycles consisting of denaturation at 95° C. for 30 s, annealing at 55° C. for 30 s, and extension at 72° C. for 1 m. The PCR products were subjected to electrophoresis in a 1.0% agarose gel, and a 1.14 kb band was eluted, purified, and treated with HindII. The pCL1920 vector including the cysK promoter was treated with EcoRV and HindIII, and the resulting restriction fragments were cloned. The plasmid expressing metX gene derived from *Pseudogulbenkiania ferrooxidans* obtained as a result of the cloning was named as "pCL-PcysK-metX (pfe)".

Example 3

Construction of Experimental Strains 3-1. Deletion of metB Gene

The metB gene encoding cystathionine gamma synthase in an wild type *E. coli* (K12) W3110 strain was deleted. For the deletion of the metB gene, the FRT-one-step-PCR deletion method was performed (PNAS (2000) vol 97: P 6640-6645). For the deletion of the metB gene, a deletion cassette was constructed by PCR using the primers of SEQ ID NOS: 6 and 7, and the pKD3 vector (PNAS (2000) vol 97: P 6640-6645) as a template.

SEQ ID NO: 6)
5'-TTACTCTGGTGCCTGACATTTCACCGACAAAGCCCAGGGAACTTCAT
CACGTGTAGGCTGGAGCTGCTTC-3'

SEQ ID NO: 7)
5'-CGCTGCGCCAGCTCCATACGCGGCACCAGCGTTCGCAACCCACGTAG
CAGCATATGAATATCCTCCTTAG-3'

The PCR was performed for 30 cycles consisting of denaturation at 95° C. for 30 s, annealing at 55° C. for 30 s, and extension at 72° C. for 1 m. The PCR products were subjected to electrophoresis in a 1.0% agarose gel, and a 1.1 kb band was eluted and purified. The recovered DNA fragment was electroporated into the *E. coli* (K12) W3110 strain, which was already transformed with the pKD46 vector (PNAS (2000) vol 97 P 6640-6645). For the electroporation, the W3110 strain, which was transformed with the pKD46, was cultured in LB medium containing 200 μg/L of ampicillin and 5 mM L-arabinose at 30° C. until $OD_{600}$ reached 0.5, and washed 3 times with 10% glycerol for use. The electroporation was performed at 2500V. The recovered strain was plated on LB plate medium containing 30 μg/L chloramphenicol, cultured at 37° C. for 1 to 2 days, and the strain showing resistance to chloramphenicol was selected. The selected strain was subjected to PCR under the same conditions described above using the primers of SEQ ID NOS: 8 and 9, and the deletion of metB gene was confirmed by observing the presence of a 1.5 kb band of the gene in a 1.0% agarose gel.

SEQ ID NO: 8)
5'-TATTCGCCGCTCCATTCAGC-3'

SEQ ID NO: 9)
5'-TACCCCTTGTTTGCAGCCCG-3'

The thus-confirmed strain was transformed with the pCP20 vector (PNAS (2000) vol 97 P 6640-6645) and cultured in LB medium containing 100 μg/L of ampicillin. The final strain with a deletion of metB gene having a reduced size, which was confirmed in a 1.0% agarose gel, was constructed by performing PCR under the same conditions and confirmed that the chloramphenicol marker was removed from the strain. The thus-constructed strain, which requires methionine, was named as "CC03-0131".

3-2. Deletion of thrB Gene

The amount of synthesis of O-succinylhomoserine from homoserine was attempted to increase by deleting the thrB gene which encodes homoserine kinase. In particular, it is essential to delete the thrB gene to use a threonine-producing strain, because the utilization activity of homoserine is very high. The deletion of the thrB gene in the CC03-0131 strain constructed above was performed by the FRT-one-step-PCR deletion method. A thrB deletion cassette was constructed by PCR using the primers of SEQ ID NOS: 10 and 11 and the pKD3 vector as a template.

SEQ ID NO: 10)
5'-CATGGTTAAAGTTTATGCCCCGGCTTCCAGTGCCAATATGAGCGTCG
GGTGTGTAGGCTGGAGCTGCTTC-3'

SEQ ID NO: 11)
5'-GGAGATACCGCTCGCTACCGCGCCGATTTCCGCGACCGCCTGCCGCG
CCTCATATGAATATCCTCCTTAG-3'

The PCR was performed for 30 cycles consisting of denaturation at 95° C. for 30 s, annealing at 55° C. for 30 s, and extension at 72° C. for 1 m. The PCR products were subjected to electrophoresis in a 1.0% agarose gel, and a 1.1 kb band was eluted and purified. The recovered DNA fragment was electroporated into the CC03-0131 strain, which was already transformed with the pKD46 vector. For the electroporation, the CC03-0131 strain, which was transformed with the pKD46, was cultured in LB medium containing 200 μg/L of ampicillin and 5 mM arabinose at 30° C. until $OD_{600}$ reached 0.5, and washed 3 times with 10% glycerol for use. The electroporation was performed at 2500V. The recovered strain was plated on LB plate medium containing 30 μg/L chloramphenicol, cultured at 37° C. for 1 to 2 days, and the strain showing resistance to chloramphenicol was selected.

The selected strain was subjected to PCR under the same conditions described above using the primers of SEQ ID NOS: 12 and 13, and the deletion of thrB gene was confirmed by observing the presence of a 1.5 kb band of the gene in a 1.0% agarose gel.

SEQ ID NO: 12)
5'-ACTCGACGATCTCTTTGCC-3'

SEQ ID NO: 13)
5'-ACGCCGAGAGGATCTTCGCAG-3'

The thus-confirmed strain was transformed with the pCP20 vector and cultured in LB medium containing 100 μg/L of ampicillin. The final strain with a deletion of thrB gene having a reduced size, which was confirmed in a 1.0% agarose gel, was constructed by performing PCR under the same conditions and confirmed that the chloramphenicol marker was removed from the strain. The thus-constructed strain was named as "CC03-0131-2".

3-3. Deletion of metA Gene

For the characterization of substrate specificity and activity of the metX gene derived from *Pseudogulbenkiania ferrooxidans* 2002 in an *E. coli* strain, the original metA gene on the chromosome was deleted based on the CC03-0131-2 strain, which is an *E. coli* (K12) W3110 strain with deletions of metB and thrB genes. The metA gene was deleted by the FRT-one-step-PCR deletion method. A metA deletion cassette was constructed by PCR using the primers of SEQ ID NOS: 14 and 15 and the pKD3 vector as a template.

```
                                                     SEQ ID NO: 14)
5'-TCAGCTGTTGCGCATCGATTCCCGTGAATCGCGCAACACGCCCGCAG
AGCGTGTAGGCTGGAGCTGCTTC-3'

SEQ ID NO: 15)
5'-CCGTCACAAAGGCAATGCGCTTATCTTTACTGGCAAACAGATATGCA
TCCCATATGAATATCCTCCTTAG-3'
```

The PCR was performed for 30 cycles consisting of denaturation at 95° C. for 30 s, annealing at 55° C. for 30 s, and extension at 72° C. for 1 m. The PCR products were subjected to electrophoresis in a 1.0% agarose gel, and a 1.1 kb band was eluted and purified. The recovered DNA fragment was electroporated into the CC03-0131-2 strain, which was already transformed with the pKD46 vector. For the electroporation, the CC03-0131-2 strain, which was transformed with the pKD46, was cultured in LB medium containing 200 μg/L of ampicillin and 5 mM arabinose at 30° C. until $OD_{600}$ reached 0.5, and washed 3 times with 10% glycerol for use. The electroporation was performed at 2500V. The recovered strain was plated on LB plate medium containing 30 μg/L chloramphenicol, cultured at 37° C. for 1 to 2 days, and the strain showing resistance to chloramphenicol was selected.

The selected strain was subjected to PCR under the same conditions described above using the primers of SEQ ID NOS: 16 and 17, and the deletion of metA gene was confirmed by observing the presence of a 1.5 kb band of the gene in a 1.0% agarose gel.

```
                                                     SEQ ID NO: 16)
5'-CTCATTAACGTTGGTTGTCA-3'

SEQ ID NO: 17)
5'-TATCTTGCTGCTGCTGAATG-3'
```

The thus-confirmed strain was transformed with the pCP20 vector and cultured in LB medium containing 100 μg/L of ampicillin. The final strain with a deletion of metA gene having a reduced size, which was confirmed in a 1.0% agarose gel, was constructed by performing PCR under the same conditions and confirmed that the chloramphenicol marker was removed from the strain. The thus-constructed strain was named as "CC03-0132".

3-4. Construction of a Strain Introduced with a Plasmid Expressing metX Gene Derived from *Pseudogulbenkiania ferrooxidans*

For the characterization of substrate specificity and activity of the metX gene derived from *Pseudogulbenkiania ferrooxidans* 2002, the CC03-0132 strain, which is an *E. coli* (K12) W3110 strain with deletions of metB, thrB and metA genes, was introduced with the plasmid pCL-PcysK-metX (pfe) constructed in Example 2.

The CC03-0132 strain introduced with the pCL-PcysK-metX (pfe) was named as "CC03-0135" and deposited at the Korean Culture Center of Microorganisms (KCCM) located at 361-221, Hongje-1-dong, Seodaemun-gu, Seoul, Korea, which is a subsidiary of the Korean Federation of Culture Collections (KFCC), recognized as an international depositary authority under the Budapest Treaty, on Jun. 10, 2013 under the Accession Number KCCM11423P.

A strain was constructed by introducing a plasmid pCL-PcysK-metA, which was constructed in the same manner as in Example 2 except that using wild type metA in the CC03-0132 strain as the control group. The thus-constructed strain was named as "CC03-0132/pCL-PcysK-metA".

Additionally, a strain was constructed using a threonine-producing strain CJM002, which was released from the methionine requirement (Accession Number: KCCM-10568), via artificial mutation using NTG based on the L-threonine-producing strain TF4076 (Accession Number: KFCC-10718), which is a methionine-requiring strain disclosed in Korean Pat. No. 10-0905381, in the same manner as in Examples 3-1 to 3-3, and the thus-constructed strain was named as "CJM-BTA".

The plasmids, pCL-PcysK-metX (pfe) and pCL-PcysK-metA, as described above, were introduced based on the CJM-BTA strain, and the thus-constructed strain was named as "CJM-BTA/pCL-PcysK-metX (pfe)" and "CJM-BTA/pCL-PcysK-metA", respectively.

Example 4

Production of O-Succinylhomoserine Using a Strain 4-1. Flask Culture Experiment

For the characterization of substrate specificity and activity of the metX gene derived from *Pseudogulbenkiania ferrooxidans* 2002, introduced into the strain constructed in Example 3, an Erlenmeyer flask culture was performed. The composition of the flask culture is shown in Table 1 below.

TABLE 1

| Composition | Stock | Concentration (per Liter) | Volume (mL) |
|---|---|---|---|
| Glucose | | 40 g | 200 |
| $KH_2PO_4$ | | 2 g | 100 |
| Ammonium sulfate | | 17 g | 500 |
| $MgSO_4·7H_2O$ | | 1 g | |
| Yeast extract | | 4 g | |
| Methionine | | 0.4 g | |
| $MnSO_4·7H_2O$ | 10 mg/mL | 0.01 g (1 mL of stock) | |
| $ZnSO_4·7H_2O$ | 1 mg/mL | 0.01 g (10 mL of stock) | |
| $FeSO_4·7H_2O$ | 10 mg/mL | 10 mg (1 mL of stock) | |
| Calcium carbonate | | 30 g | 200 |

The CC03-0132 strain and the CJM-BTA strain were inoculated into LB plate medium as control groups. The CC03-0135 strain (transformed with a metX expression vector), the CC03-0132/pCL-PcysK-metA strain (transformed with the metA expression vector prepared using the same vector), and two other strains, CJM-BTA/pCL-PcysK-metX (pfe) and CJM-BTA/pCL-PcysK-metA (transformed with the metX expression vector or the metA expression vector based on the CJM-BTA strain, respectively) were inoculated into LB plate media containing spectinomycin, cultured at 33° C. overnight. Then, single colonies were inoculated into 2 mL of LB medium containing spectinomycin, cultured at 33° C. for 2 hours, inoculated again into a 250 mL Erlenmeyer containing 25 mL of flask medium to an absorbance of 0.07 at OD600, cultured at 33° C. at a rate of 200 rpm for 48 hours, and the amount of O-succinylhomoserine production was compared via HPLC analysis. The results are shown in Table 2 below.

TABLE 2

| Strain | OD | Glucose consumption (g/L) | Amount of O-succinylhomoserine production (g/L) |
|---|---|---|---|
| CC03-0132 | 16 | 40 | 0.0 |
| CC03-0132/ pCL-PcysK-metA | 20 | 40 | 0.5 |

TABLE 2-continued

| Strain | OD | Glucose consumption (g/L) | Amount of O-succinylhomoserine production (g/L) |
|---|---|---|---|
| CC03-0132/ pCL-PcysK-metX (pfe): CC03-0135 | 21 | 40 | 1.5 |
| CJM-BTA | 5 | 40 | 0.0 |
| CJM-BTA/ pCL-PcysK-metA | 6 | 40 | 1.0 |
| CJM-BTA/ pCL-PcysK-metX (pfe) | 7 | 40 | 4.0 |

As a result, it was confirmed that the metX gene derived from *Pseudogulbenkiania ferrooxidans* 2002, as is the case with the metA gene of *E. coli*, produces O-succinylhomoserine using succinyl-CoA as a substrate but did not produce O-acetylhomoserine. When the metX gene derived from *Pseudogulbenkiania ferrooxidans* 2002 was introduced, no feedback inhibition by the methionine added to the medium appeared even with the wild type itself without introduction of any modification.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

---

The invention claimed is:

1. An isolated polynucleotide comprising the nucleotide sequence as set forth in SEQ ID NO: 3.

2. An O-succinylhomoserine-producing *Escherichia* sp. microorganism expressing a polypeptide having a resistance to feedback inhibition by methionine and a homoserine succinyltransferase activity, wherein the polypeptide has the amino acid sequence as set forth in SEQ ID NO: 1.

3. The *Escherichia* sp. microorganism of claim 2, wherein the *Escherichia* sp. microorganism is *Escherichia coli*.

4. The *Escherichia* sp. microorganism of claim 2, wherein the metB gene encoding cystathionine gamma synthase is further deleted or weakened.

5. The *Escherichia* sp. microorganism of claim 2, wherein the thrB gene encoding homoserine kinase or the metA gene encoding homoserine O-succinyltransferase are further deleted or weakened.

6. The *Escherichia* sp. microorganism of claim 2, wherein SEQ ID NO: 1 is encoded by SEQ ID NO: 2 or 3.

7. A method of producing O-succinylhomoserine, comprising: (a) culturing the microorganism of claim 2 in a medium; and (b) obtaining O-succinylhomoserine from the microorganism or the medium.

8. A method of producing O-succinylhomoserine, comprising: (a) culturing the microorganism of claim 3 in a medium; and (b) obtaining O-succinylhomoserine from the microorganism or the medium.

9. A method of producing O-succinylhomoserine, comprising: (a) culturing the microorganism of claim 4 in a medium; and (b) obtaining O-succinylhomoserine from the microorganism or the medium.

10. A method of producing O-succinylhomoserine, comprising: (a) culturing the microorganism of claim 5 in a medium; and (b) obtaining O-succinylhomoserine from the microorganism or the medium.

* * * * *

SEQUENCE LISTING

<160> NUMBER OF SEQ ID NOS: 17

<210> SEQ ID NO 1
<211> LENGTH: 380
<212> TYPE: PRT
<213> ORGANISM: Pseudogulbenkiania ferrooxidans

<400> SEQUENCE: 1

```
Met Ser Thr Thr Glu Ser Ser Val Gly Ile Val Ser Ala Gln Gln Ala
1               5                   10                  15

Leu Phe Asp Val Pro Leu Asp Leu Ala Cys Gly Lys Thr Leu Thr Ser
                20                  25                  30

Tyr Gln Leu Ile Phe Glu Thr Tyr Gly Glu Leu Asn Ala Ala Lys Ser
            35                  40                  45

Asn Ala Ile Leu Ile Cys His Ala Leu Ser Gly His His Ala Ala
        50                  55                  60

Gly Arg Tyr Gln Pro Asp Asp Lys Ser Ala Gly Trp Trp Asp Ser Met
65                  70                  75                  80

Ile Gly Pro Gly Lys Pro Ile Asp Thr Arg Arg Phe Phe Val Val Ala
                85                  90                  95

Leu Asn Asn Leu Gly Gly Cys His Gly Ser Thr Gly Pro Ser Ser Ile
                100                 105                 110

Asn Pro Ala Thr Arg Gln Pro Trp Gly Ser Ala Phe Pro Val Val Thr
            115                 120                 125

Val Pro Asp Trp Val Thr Ala Gln Ala Arg Leu Ala Asp Arg Leu Gly
        130                 135                 140

Ile Asp Arg Trp Ala Ala Ile Ile Gly Gly Ser Leu Gly Gly Met Gln
145                 150                 155                 160

Ala Leu Gln Trp Ser Ile Asp Tyr Pro Asp Arg Val Ala Asn Ala Ile
                165                 170                 175

Val Ile Ala Ser Ala Pro Lys Leu Ser Ala Gln Asn Ile Ala Phe Asn
                180                 185                 190

Asp Val Ala Arg Gln Ala Ile Leu Thr Asp Pro Asp Phe His Gly Gly
            195                 200                 205

Asp Phe Tyr Gln Gln Asp Ala Ile Pro Arg Arg Gly Leu Arg Leu Ala
        210                 215                 220

Arg Met Leu Gly His Ile Thr Tyr Leu Ser Asp Asp Gly Met Gly Glu
225                 230                 235                 240

Lys Phe Gly Arg Met Leu Arg Ser Gly Glu Tyr Lys Phe Gly Tyr Asp
                245                 250                 255
```

```
Val Glu Phe Glu Ile Glu Ser Tyr Leu Arg Tyr Gln Gly Asp Lys Phe
            260                 265                 270

Ser Asp Tyr Phe Asp Ala Asn Thr Tyr Leu Leu Met Thr Lys Ala Leu
        275                 280                 285

Asp Tyr Phe Asp Pro Ala Lys Asp His Gly Gly Asp Leu Val Ala Ala
        290                 295                 300

Leu Lys Lys Ala Thr Ala Asn Phe Leu Val Ala Ser Phe Thr Ser Asp
305                 310                 315                 320

Trp Arg Phe Ser Pro Leu Arg Ser Arg Glu Leu Val Gln Gly Leu Ile
                325                 330                 335

Ala Ala Asp Lys Arg Val Ala Tyr Gly Glu Ile Glu Ser Ala His Gly
            340                 345                 350

His Asp Ala Phe Leu Met Thr Asp Gln Pro Tyr Val Asp Leu Met Arg
        355                 360                 365

Ala Tyr Leu Asp Arg Val Ala Lys Glu Val Ala Ala
        370                 375                 380

<210> SEQ ID NO 2
<211> LENGTH: 1143
<212> TYPE: DNA
<213> ORGANISM: Pseudogulbenkiania ferrooxidans

<400> SEQUENCE: 2
atgtccacaa ccgaatcgtc ggtcggtatc gtcagcgccc agcaggcgct gttcgacgtg      60
ccgctcgatc tggcctgcgg caagacgctg acgtcgtacc agctgatttt tgagacctac     120
ggcgagctga acgccgccaa gagcaacgcc atcctgatct gccacgcgtt gtccggccac     180
caccacgccg ccggccgcta ccagccggac gacaagagcg ccggctggtg ggacagcatg     240
atcgggccgg gcaagccgat cgacacgcgc cgcttcttcg tggtggcgct caacaacctg     300
ggcggctgcc acggttctac tggcccctcc agcatcaacc cggccacgcg ccagccgtgg     360
ggctcggcct tcccggtggt gacggtgccg gactgggtga cggcgcaggc gcggttggcc     420
gaccggctcg gcatcgaccg ctgggcggcg atcatcggcg gctcgctcgg cggcatgcag     480
gcgctgcagt ggagcatcga ctaccccgac cgcgtcgcca acgccatcgt catcgcctcg     540
gcgcccaagt tgtcggcgca gaacatcgcc ttcaacgacg tggcgcgcca ggccatcctc     600
accgacccgg acttccacgg cggcgacttc taccagcagg atgccatccc cgtcgcggc     660 ctgcgcctgg cgcgcatgct gggccacatc acctatctgt cggacgacgg catgggcgag     720
aaattcggcc gcatgctgcg ctccggcgag tacaagttcg gctacgacgt ggagttcgag     780
atcgagtcct acctgcgcta ccagggcgac aagttctccg actacttcga cgccaacacc     840
tacctcttga tgaccaaggc gctggactac ttcgatccgg ccaaggacca cggcggcgac     900
ctggtggcgg cgctgaagaa ggcgaccgcc aacttcctgg tggcgagctt cacttccgac     960
tggcgcttct cgcccttgcg ctcgcgcgag ctggtgcagg gcctgatcgc cgccgacaag    1020
cgcgtggcct acggcgagat cgaatccgcc cacggccacg acgccttcct gatgaccgac    1080
caaccctacg tggacctgat gcgtgcctac ctcgaccgtg tagccaagga ggtggcggca    1140
tga                                                                  1143

<210> SEQ ID NO 3
<211> LENGTH: 1143
<212> TYPE: DNA
<213> ORGANISM: Pseudogulbenkiania ferrooxidans

<400> SEQUENCE: 3
```

-continued

```
atgtccacta cagaatcctc ggtcggtata gtcagcgccc agcaggcgct gtttgacgtg      60
cctctcgatc tggcttgcgg gaagacgctg acatcttatc agttaatttt cgaaacctac     120
ggcgagctga atgcagccaa aagcaatgcc atcctgattt gtcatgcctt gtccggacac     180
caccatgccg ccggccggta tcagcccgat gacaaatcag cgggatggtg ggactcaatg     240
atcgggccgg gcaaaccgat agacactaga cgcttttttcg tggtcgcact caataacctg    300
ggcgggtgtc acggttctac gggcccttcg agcataaatc cggctacgcg ccagccgtgg     360
gggtctgcat ttccagtggt aacggttcct gattgggtta ctgcgcaggc acggcttgct     420
gatcggctcg gtatagatcg ctgggcagcg attatcggag gttcactagg cggtatgcaa     480
gcactgcagt ggagcattga ttaccccgat cgcgtagcaa atgccattgt catcgccagt     540
gcacccaaat tgtcggcaca aaacattgcc tttaacgacg tggcgcgaca agcaattta      600
accgatcctg actttcatgg cggcgatttt taccaacaag atgccattcc gcgtcgcggc     660
ctgagactgg ctcgtatgct gggccacatt acctatctgt ctgatgacgg catgggagaa     720
aaatttggtc gcatgctgag aagtggggaa tataaattcg gctatgacgt ggaatttgaa     780
attgagagtt atctacgcta tcagggtgat aaattctccg attattttga tgccaacaca     840
tacttattga tgacaaaagc ccttgactat ttcgatcctg ccaaggatca tggtggcgat     900
ttagtggctg ctctgaaaaa agcgaccgca aattttttag ttgcgtcatt tactagcgat     960
tggcgcttta gtccattgcg tagtagggag ctggtgcaag gtcttatcgc cgccgacaag   1020
cgagtagcct atgagaaat  cgagtcagcc catggccatg atgcgtttct gatgaccgac   1080
cagccatatg tcgacctgat gcgtgcctat cttgaccgtg tagccaaaga agtggcggca   1140
taa                                                                  1143
```

```
<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
atcatgtcca ctacagaatc ctcg                                             24

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
cccaagcttt tatgccgcca cttctttggc                                       30

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
ttactctggt gcctgacatt tcaccgacaa agcccaggga acttcatcac gtgtaggctg      60
gagctgcttc                                                             70
```

-continued

```
<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
cgctgcgcca gctccatacg cggcaccagc gttcgcaacc cacgtagcag catatgaata      60
tcctccttag                                                             70

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tattcgccgc tccattcagc                                                  20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
taccccttgt ttgcagcccg                                                  20

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10
catggttaaa gtttatgccc cggcttccag tgccaatatg agcgtcgggt gtgtaggctg      60
gagctgcttc                                                             70

<210> SEQ ID NO 11
<211> LENGTH: 70
<212> TYPE: DNA
<213> ORGANISM: Artificial Sequence
<220> FEATURE:
<223> OTHER INFORMATION: primer

<400> SEQUENCE: 11
ggagataccg ctcgctaccg cgccgatttc cgcgaccgcc tgccgcgcct catatgaata      60
tcctccttag                                                             70

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
actcgacgat ctctttgcc                                                   19
```

```
<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
acgccgagag gatcttcgca g                                              21

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
tcagctgttg cgcatcgatt cccgtgaatc gcgcaacacg cccgcagagc gtgtaggctg    60
gagctgcttc                                                           70

<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
ccgtcacaaa ggcaatgcgc ttatctttac tggcaaacag atatgcatcc catatgaata    60
tcctccttag                                                           70

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
ctcattaacg ttggttgtca                                                20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tatcttgctg ctgctgaatg                                                20
```